United States Patent
Nguyen-Kim et al.

(10) Patent No.: US 10,202,486 B2
(45) Date of Patent: Feb. 12, 2019

(54) POLY(OXYALKYLENE)URETHANES AS A SOLUBILIZER AND STABILIZER IN ACTIVE INGREDIENT FORMULATIONS

(71) Applicant: BASF SE, Ludwigshafen (DE)

(72) Inventors: Viet Nguyen-Kim, Heidelberg (DE); Murat Mertoglu, Ludwigshafen (DE); Ann-Kathrin Marguerre, Heidelberg (DE); Volodymyr Boyko, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/902,888

(22) PCT Filed: Jul. 7, 2014

(86) PCT No.: PCT/EP2014/064394
§ 371 (c)(1),
(2) Date: Jan. 5, 2016

(87) PCT Pub. No.: WO2015/004037
PCT Pub. Date: Jan. 15, 2015

(65) Prior Publication Data
US 2016/0152762 A1 Jun. 2, 2016

(30) Foreign Application Priority Data

Jul. 10, 2013 (EP) .................... 13175995

(51) Int. Cl.
| | | |
|---|---|---|
| C08G 18/48 | (2006.01) | |
| C08G 18/75 | (2006.01) | |
| C08G 18/83 | (2006.01) | |
| A01N 25/30 | (2006.01) | |
| C08G 18/08 | (2006.01) | |
| C08G 18/10 | (2006.01) | |
| C08G 18/28 | (2006.01) | |
| C08G 18/34 | (2006.01) | |
| A01N 43/56 | (2006.01) | |

(52) U.S. Cl.
CPC ......... *C08G 18/4854* (2013.01); *A01N 25/30* (2013.01); *A01N 43/56* (2013.01); *C08G 18/0804* (2013.01); *C08G 18/10* (2013.01); *C08G 18/2825* (2013.01); *C08G 18/2865* (2013.01); *C08G 18/348* (2013.01); *C08G 18/755* (2013.01); *C08G 18/833* (2013.01)

(58) Field of Classification Search
CPC .. C08G 18/10; C08G 18/2825; C08G 18/348; C08G 18/0804; C08G 18/2865; C08G 18/4854; C08G 18/755; C08G 18/833; A01N 25/30; A01N 43/56
USPC .......................................... 504/100; 514/406
See application file for complete search history.

(56) References Cited

U.S. PATENT DOCUMENTS 4,155,892 A  5/1979  Emmons et al.
2011/0275757 A1  11/2011  Schönberger et al.

FOREIGN PATENT DOCUMENTS

| WO | WO 1998005205 | 2/1998 | | |
|---|---|---|---|---|
| WO | WO 2007145399 | 12/2007 | | |
| WO | WO 2010083960 | 7/2010 | | |
| WO | WO 2010083960 A1 * | 7/2010 | ......... | C08G 18/0828 |
| WO | WO 2010145913 | 12/2010 | | |
| WO | WO 2010145913 A1 * | 12/2010 | ............ | B01F 17/005 |

OTHER PUBLICATIONS

Furer et al., Pestic. Sci.; 1977, 8, 337-344.*
International Preliminary Report on Patentability, issued in PCT/EP2014/064394, dated Oct. 30, 2015.
International Search Report, issued in PCT/EP2014/064394, dated Aug. 6, 2014.
Search Report, issued in corresponding EP Application No. 13175995, dated Jan. 3, 2014.

* cited by examiner

*Primary Examiner* — Carlos A Azpuru
*Assistant Examiner* — Courtney A Brown
(74) *Attorney, Agent, or Firm* — Brinks Gilson & Lione

(57) ABSTRACT

Poly(oxyalkylene)urethane surfactants of the formula (I)

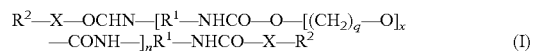

in which
$R^1$: an alkylene radical, a cycloalkylene radical or an arylene radical;
X: —O— or —NH—;
$R^2$: a linear or branched ($C_1$-$C_4$)-alkyl radical, monosubstituted by a group selected from: sulfo, carboxyl and [N,N-di-($C_1$-$C_4$)-alkyl]amino, or disubstituted by: carboxyl; carboxyl and hydroxyl; carboxyl and mercapto; or, if X=—O—, $R^2$ may also be defined as [$R^3$—O—CONH—$R^1$—NHCO—O—]$_m R^4$ in which
$R^3$: a linear or branched ($C_1$-$C_4$)-alkylene radical, monosubstituted by COOH, especially a —$CH_2$—[C(COOH)($CH_3$)]—$CH_2$— radical,
$R^1$ is as defined above, and
$R^4$: $C_2$-$C_{22}$-alkyl or a —$CH_2$—[C(COOH)($CH_3$)]—$CH_2$—OH radical, and
m=an integer from 1 to 10;
n=an integer from 1 to 7;
q=an integer from 3 to 5; and
x=an integer from 10 to 70;
and the water-soluble or water-dispersible salts thereof are described as a solubilizer and stabilizer in active ingredient formulations.

20 Claims, No Drawings

POLY(OXYALKYLENE)URETHANES AS A SOLUBILIZER AND STABILIZER IN ACTIVE INGREDIENT FORMULATIONS

This application is a National Stage application of International Application No. PCT/EP2014/064394, filed Jul. 7, 2014. This application also claims priority under 35 U.S.C. § 119 to European Patent Application No. 13175995.3, filed Jul. 10, 2013.

DESCRIPTION

The present invention provides poly(oxyalkylene)urethane surfactants of the formula (I) and a process for preparation thereof, as described below. The invention further relates to a composition comprising the poly(oxyalkylene)urethane surfactant and a sparingly water-soluble active ingredient. It further relates to the use of the poly(oxyalkylene)urethane surfactant for solubilization of a sparingly water-soluble active ingredient in aqueous formulations. It further relates to the use of the poly(oxyalkylene)urethane surfactant for solubilization of a sparingly water-soluble active ingredient in oily formulations. The invention also relates to the use of the poly(oxyalkylene)urethane surfactants in an agrochemical formulation comprising the poly(oxyalkylene)urethane surfactant and a sparingly water-soluble pesticide for control of phytopathogenic fungi and/or unwanted vegetation and/or unwanted insect or mite infestation and/or for regulation of the growth of plants, and finally to seed comprising the poly(oxyalkylene)urethane surfactant.

In many cases, it is necessary to solubilize hydrophobic active ingredients in water without chemically altering the active ingredient in question as such. For this purpose, it is possible, for example, to produce an emulsion, in which case the active ingredient in question is present in the oil phase of the emulsion. For many active pharmaceutical ingredients or especially crop protection compositions, especially for those which are to be transported with a body fluid or in a plants sap, such a procedure, however, is not possible. Emulsions can break under the action of high shear forces. In addition, sterilization is not possible with retention of the emulsion in many cases, for example for active pharmaceutical ingredients.

WO 2010/083960 relates to surfactants based on polyurethanes with alkylene oxide units. The polyurethanes are prepared by reaction of polyisocyanate prepolymers with a monohydric polyether alcohol. The prepolymers are preferably reaction products of diisocyanates different types of polyols, preferably polyetherpolyols. The prepolymers can additionally comprise organic di-or polyamines or alkanolamines. The polyurethanes are in particular used as foam stabilizers in polymers.

WO 2010/145913 discloses a dispersant which is the reaction product of a polyisocyanate with a monoalkylether of a polyoxyalkylenemonoamine.

WO 98/05205 refers to a pesticidal composition comprising a pesticide and hydrophilic polyurethane. The hydrophilic polyurethane is the reaction product of oxy-C2-C4-alkylene based-diols or polyols with di-and polyfunctional isocayanates. The hydrophilic isocyanate end-capped prepolymers can be further reacted with surfactants via a covalent linkage between the isocyanate group and the reactive group available on the surfactant. Preferably the surfactant is an alkyl ethoxylated amine.

WO 2007/145399 describes a poly(oxyalkylene) surfactant which is obtained by a first reaction of a polyisocyanate compound with polyethylene glycol, and then a further reaction of the reaction product with a monoalcohol having 8 to 36 carbon atoms.

U.S. Pat. No. 4,155,892 relates to poly(oxyalkylene) urethanes with terminal hydrophobic groups preferably containing 4-20 carbon atoms based on aliphatic or aromatic monohydroxy or monoamino compounds. The poly(oxyalkylene) urethanes can be used in aqueous compositions comprising a pesticidal or pharmaceutical active ingredient.

The use of amphiphilic polymers as dispersants increased the solubility of sparingly water-soluble active ingredients in agrochemical and pharmaceutical aqueous formulations. In this context, for example, propylene oxide (PO)-ethylene oxide (EO) block copolymers, called poloxamers, having a molecular weight above 1000 have been found to be useful (U.S. 2006/0013871, WO 95/01722 inter alia). Poloxamers of this kind are poly(a-oxyethylene-b-oxypropylene-a-oxyethylene) triblock copolymers and are commercially available as Pluronics® (®=trademark registered to BASF). However, the solubilization capacity of the aforementioned block copolymers with respect to hydrophobic active ingredients is still in need of improvement.

It is therefore an object of the present invention to provide dispersants which have an improved solubilization capacity for sparingly water-soluble active ingredients in aqueous or oily formulations of the active ingredients. It is a further object of the invention to provide stable aqueous or oily compositions comprising the dispersant and a sparingly water-soluble active ingredient.

The objects were achieved by the inventive poly(oxyalkylene)urethane surfactant of the formula (I) as described below.

The invention provides a poly(oxyalkylene)urethane surfactant of the formula (I)

$$R^2—X—OCHN—[R^1—NHCO—O—[(CH_2)_q—O]_x—CONH—]_nR^1—NHCO—X—R^2 \quad (I)$$

in which $R^1$: an alkylene radical, a cycloalkylene radical or an arylene radical;

X: —O— or —NH—;

$R^2$: a linear or branched $(C_1$-$C_4)$-alkyl radical, monosubstituted by a group selected from: sulfo, carboxyl and [N,N-di-$(C_1$-$C_4)$-alkyl]amino, or disubstituted by: carboxyl; carboxyl and hydroxyl; carboxyl and mercapto; or, if X=—O—, $R^2$ may also be defined as $[R^3$—O—CONH—$R^1$—NHCO—O—$]_mR^4$ in which $R^3$: a linear or branched $(C_1$-$C_4)$-alkylene radical, monosubstituted by COOH, especially a —$CH_2$—[C(COOH)(CH_3)]—$CH_2$— radical, $R^1$ is as defined above, and $R^4$: $C_2$-$C_{22}$-alkyl or a —$CH_2$—[C(COOH)(CH_3)]—$CH_2$—OH radical, and m=an integer from 1 to 10;

n=an integer from 1 to 7;

q=an integer from 3 to 5; and x=an integer from 10 to 70;

and the water-soluble or water-dispersible salts thereof.

The linear or branched substituted (C1-C4)-alkyl radical $R^2$ preferably has one of the aforementioned substituents at the terminal carbon atom. If the alkyl radical $R^2$ is disubstituted, the substituents are preferably on different carbon atoms in the alkyl radical, one substituent preferably being at the terminal carbon atom.

Combinations of preferred features with other preferred features are encompassed by the present invention.

Suitable alkylenes $R^1$ are, for example, alkylenes having 4 to 12 carbon atoms, such as 1,4-butylenediyl, 1,12-dodecamethylenediyl, 1,10-decamethylenediyl, 2-butyl-2-ethylpentamethylene-1,5-diyl, 2,4,4- or 2,2,4-trimethylhexamethylene-1,6-diyl, and especially hexamethylenediyl (hexane-1,6-diyl).

The cycloalkylenes $R^1$ have generally 6 to 12 carbon atoms. The cycloalkylenes $R^1$ may optionally be substituted by one or more alkyl or alkylene radicals. Preference is given to cyclohexyl radicals, which are optionally substituted by one or more alkyl or alkylene radicals. Examples of suitable cycloalkylenes $R^1$ include: isophoronediyl, 2-(propylen-3-yl)cyclohexyl-1-yl, 4-methylcyclohexane-1,3-diyl and 1,3-di(methylene)cyclohexane. It is also possible to use, as cycloalkylene $R^1$, the following radicals of what is called $H_{12}$-MDI or diisocyanates called "saturated MDI": for example dicyclohexymethane-4,4'-diyl or dicyclohexylmethane-2,4'-diyl. Isophoronediyl is very particularly preferred. Isophoronediyl is understood to mean (3-methylene)-3,5,5-trimethylcyclohexan-1-yl.

In addition, $R^1$ may also be, although less preferably, an arylene radical, which may be substituted by one or more alkyl or alkylene radicals. Examples of suitable arylene radicals are tolylene-2,4- and/or -2,6-diyl, diphenylmethane-4,4'-, -2,4'- and/or -2,2'-diyl, and polyphenylpolymethylene-polyyl radicals.

In the formula (I), the $R^1$ radicals may independently be the same or different.

In the polyoxyalkylene block $[(CH_2)_q—O]_x$ present in formula (I), q is generally an integer from 3 to 5, especially q=4. x is generally an integer from 10 to 70, especially from 13 to 28. The $C_3$ to $C_5$-alkylene is preferably independently propylene, butylene or pentylene, especially n-butylene, or a mixture of a plurality of these groups. The aforementioned alkylene radicals may be present individually or in mixtures of a plurality of different alkylene radicals. For example, propylene and butylene radicals may be mixed. The various alkylene radicals may be present in random sequence or in block form.

Preferably, n-butylene is present alone.

The substituted linear or branched $(C_1-C_4)$-alkyl radical $R^2$ may be a substituted methyl, ethyl, n-propyl, isopropyl, n-, sec-, iso- or tert-butyl radical; preferably, $R^2$ is a substituted ethyl or methyl radical.

In a first embodiment (A-I), in the formula (I), the $R^2$ radical is a linear or branched $(C_1-C_4)$-alkyl radical, especially an ethyl or methyl radical, which is monosubstituted by a group selected from: sulfo, carboxyl and [N,N-di-($C_1$-$C_2$)-alkyl]amino, or which is disubstituted by carboxyl, where the other radicals X, $R^1$, n, q, and x are each as defined above and the substituents may also be in ionic form.

Preference is given to the aforementioned inventive poly(oxyalkylene)urethane surfactants of the formula (I) in which, in addition, X=—NH—, q=4, $R^1$=isophoronediyl, n=1 to 7 and x=13 to 28.

In embodiment (A-I), particular preference is given to a poly(oxyalkylene)urethane surfactant of the formula (I) in which
X=—NH—, q=4, $R^1$=isophoronediyl, n=1 to 7, x=13 to 28 and
$R^2$ is one of the following moieties: sulfonato-2-ethyl, carboxymethyl, carboxylatomethyl, 1,2-dicarboxylatoethyl, N,N-dimethyl-2-aminoethyl and the ammonium ion thereof.

In a second embodiment (A-II), in the formula (I), the $R^2$ radical is a linear or branched $(C_1-C_4)$-alkyl radical, preferably a $(C_2-C_4)$-alkyl radical, for example an ethyl, n-propyl, isopropyl, n-butyl, sec-butyl or tert-butyl radical, more preferably an isopropyl, sec-butyl, isobutyl or tert-butyl radical, most preferably a tert-butyl radical which is monosubstituted by carboxyl or N,N-di(methyl)amino, or which is disubstituted by: carboxyl, carboxyl and hydroxyl; or,
if X=—O—, $R^2$=[$R^3$—O—CONH—$R^1$—NHCO—O—]$_m$ $R^4$ in which
$R^3$=—CH$_2$—[C(COOH)(CH$_3$)]—CH$_2$—,
$R^4$=$C_2$ to $C_{22}$-alkyl, especially $C_{12}$ to $C_{22}$-alkyl, or a —CH$_{12}$—[C(COOH)(CH$_3$)]—CH$_2$—OH radical, and
m=an integer from 1 to 10, preferably 1 to 5, more preferably from 1 to 3;
where the $R^1$, n, q, and x radicals are each as defined above and the substituents may also be in ionic form.

In embodiment (A-II), preference is given to aforementioned poly(oxyalkylene)urethane surfactants of the formula (I) in which, in addition, q=4, $R^1$=isophoronediyl, n=1 to 7, x=10 to 70, especially 13 to 28, and $R^2$ is an isopropyl, sec-butyl, isobutyl or tert-butyl radical, especially a tert-butyl radical which is disubstituted by: carboxyl and hydroxyl, or, if X=—O—, $R^2$=[$R^3$—O—CONH—$R^1$—NHCO—O—]$_m R^4$ in which=1 to 5 and $R^1$, $R^3$ and $R^4$ are each as defined above.

In embodiment (A-II), particular preference is given to poly(oxyalkylene)urethane surfactants of the formula (I) in which X=O, $R^2$ is —CH$_2$—[C(COOH)(CH$_3$)]—CH$_2$—OH or [$R^3$—O—CONH—$R^1$—NHCO—O—]$_m R^4$ in which m=1 to 3, $R^4$ =C-$_{12}$-C$_{22}$-alkyl or a —CH$_2$—[C(COOH)(CH$_3$)]—CH$_2$—OH radical, and the $R^1$, $R^2$, $R^3$, n, q, and x radicals are each as defined above.

In this second embodiment (A-II), very particular preference is given to a poly(oxyalkylene)urethane surfactant of the formula (I) in which
X=—O—, q=4, $R^1$=isophoronediyl, n=1 to 7, x=10 to 70, especially 13 to 28, and —$R^2$ is one of the following moieties: —CH$_2$—[C(COOH)(CH$_3$)]—CH$_2$—OH, —CH$_2$—[C(COOH)(CH$_3$)]—CH$_2$—O—CONH—$R^1$—NHCO—O—(C$_{12}$-C$_{22}$)-alkyl, —CH$_2$—[C(COOH)(CH$_3$)]—CH$_2$—O—CONH—$R^1$—NHCO—O—CH$_2$—[C(COOH)(CH$_3$)]—CH$_2$—OH and the corresponding ionic derivatives thereof.

The salts of the poly(oxyalkylene)urethane surfactant of the formula (I) are water-soluble or water-dispersible salts. The person skilled in the art selects the type of acid or base used for neutralization according to the desired end use.

The sulfonates are preferably alkali metal salts, especially sodium sulfonate. In aqueous formulations, the carboxylates are likewise preferably alkali metal salts, for example sodium carboxylate, and the quaternized ammonium salts of the amines are, for example, lactates or chlorides. For neutralization of carboxyl groups in oily formulations, preference is given to using bases such as aminomethylpropanol (AMP) or triethylamine.

The number-average molar mass of the poly(oxyalkylene) urethane surfactant of the formula (I) is usually in the range from 2000 to 10 000 g/mol and preferably from 3000 to 6000 g/mol (measured by means of GPC, in dimethylacetamide with PTHF as standard).

The invention further provides a process for preparing the poly(oxyalkylene)urethane surfactants of the formula (I)

$$R^2—X—OCHN—[R^1—NHCO—O—[(CH_2)_q—O]_x—CONH—]_n R^1—NHCO—X—R^2 \qquad (I)$$

in which $R^1$, $R^2$, —X—, q, x and n are each as defined above, which comprises a) reacting at least one diisocyanate OCN—R$^1$—NCO with at least one polyetherdiol HO—[(CH$_2$)$_q$—O]$_x$—H in a polar aprotic solvent to give a polyurethane; and b1) reacting the polyurethane obtained with a preferably terminally functionalized amine or alcohol of the formula NH$_2$—R$^2$ or HO—R$^2$, and b2) optionally, if the alkyl radical R$^2$ of the alcohol HO-R$^2$ is a di-carboxyl- and -hydroxyl-substituted (C$_1$-C$_4$)-alkyl radical, reacting the functionalized polyurethane with further diisocyanate OCN—R$^1$—NCO and an alkyl alcohol.

The at least one polyetherdiol used in step a) has a weight-average molar mass M$_w$ in the range from 500 to 5000 g/mol, preferably from 700 to 3000 g/mol and more preferably from 1000 to 2000 g/mol. Preferably, the polyetherdiol used in the process according to the invention is polytetrahydrofuran (=polyTHF).

The reaction of the polyetherdiols and diisocyanates in step a) is preferably effected with a molar excess of the diisocyanates.

Suitable aliphatic diisocyanate radicals R$^1$ are, for example, alkylene diisocyanates having 4 to 12 carbon atoms in the alkylene radical, such as butylene 1,4-diisocyanate, dodecamethylene 1,12-diisocyanate, decamethylene 1,10-diisocyanate, 2-butyl-2-ethylpentamethylene diisocyanate, 2,4,4- or 2,2,4-trimethylhexamethylene diisocyanate and especially hexamethylene diisocyanate (hexane 1,6-diisocyanate, HDI).

Examples of suitable cycloaliphatic diisocyanates R$^1$ include: isophorone diisocyanate (IPDI), 2-isocyanatopropylcyclohexyl isocyanate, 4-methylcyclohexane 1,3-diisocyanate (H-TDI) and 1,3-bis(isocyanatomethyl)cyclohexane. It is also possible for what is called H$_{12}$-MDI or diisocyanates called "saturated MDI", for example 4,4'-methylenebis(cyclohexyl isocyanate) (alternatively also called dicyclohexylmethane 4,4'-diisocyanate) or 2,4'-methylenebis(cyclohexyl isocyanate) to be present as radicals in the inventive polyurethanes. Isophorone diisocyanate (IPDI) is very particularly preferred.

In addition, it is also possible, although less preferred, to use aromatic di- and polyisocyanates. Examples thereof are tolylene 2,4- and 2,6-diisocyanate and the corresponding isomer mixtures, diphenylmethane 4,4'-, 2,4'- and 2,2'-diisocyanate and the corresponding isomer mixtures, mixtures of diphenylmethane 4,4'- and 2,4'-diisocyanates, polyphenylpolymethylene polyisocyanates, mixtures of diphenylmethane 4,4'-, 2,4'- and 2,2'-diisocyanates and polyphenylpolymethylene polyisocyanates (crude MDI) and mixtures of crude MDI and tolylene diisocyanates.

The organic diisocyanates and polyisocyanates can be used individually or in the form of their mixtures.

Preferably, the molar ratio of NCO groups in the diisocyanate to OH groups in the polyether polyol before the polyaddition is 2:1 to 10:9, preferably 3:2 to 6:5.

Step a) is effected in a polar aprotic solvent such as acetone, ethyl acetate, methyl ethyl ketone or mixtures thereof. The polar aprotic solvent used in accordance with the invention may alternatively also be a polar aprotic oil of a fatty acid ester or fatty acid amide of saturated fatty acids, preferably of fatty acids having 8 to 14 carbon atoms, for example N,N-dimethyldodecanamide.

It is also possible to use homogeneous mixtures of the aforementioned solvents.

The concentration of the reactants in the solvent is typically 80%.

The conversion to the polyurethane (=polyaddition) is generally effected at a temperature in the range from 70 to 90° C., preferably in the range from 75 to 85° C. The duration of the polyaddition is generally 1 to 6 and preferably 2 to 4 hours.

In a first embodiment (V-I), which is especially suitable for preparation of the poly(oxyalkylene)urethane surfactants of the formula (I) as per (A-I), in which R$^2$ is a linear or branched (C$_1$-C$_4$)-alkyl radical, especially an ethyl or methyl radical, which is monosubstituted by a group selected from: sulfo, carboxyl and [N,N-di-(C$_1$-C$_2$)-alkyl] amino, or which is disubstituted by carboxyl, where the other radicals X, R$^1$, n, q, and x are each as defined above and the substituents may also be in ionic form, step a) is preferably effected in a polar aprotic solvent such as acetone, ethyl acetate or methyl ethyl ketone. Step b1) is generally effected at a temperature in the range from 10 to 50° C., preferably in the range from 20 to 40° C.

In step b1), the reaction of the preferably terminally functionalized amine or alcohol with the polyurethane obtained in step a) is effected generally within 10 to 50 and preferably within 20 to 40 minutes. The amine is advantageously added in aqueous solution. The molar ratio of the NCO-terminated polyurethane block to the functionalized amine or alcohol in step b1) is generally 1:1.

Suitable terminally functionalized amines or alcohols for this first embodiment (V-I) are, for example, sodium taurinate, sodium glycinate, sodium aspartate and N,N-dimethylethylenediamine.

Thereafter, the polar aprotic solvent can be removed by customary methods, which gives the inventive poly(oxyalkylene)urethane surfactant of the formula (I). It has been found to be useful to remove the solvent by distillation, for example with the aid of a rotary evaporator.

The isolated inventive poly(oxyalkylene)urethane surfactant of the formula (I) can be dispersed in water and in that case is present generally as a 20-50% aqueous dispersion.

In an alternative second embodiment (V-II), the above-described process according to the invention for preparing the poly(oxyalkylene)urethane surfactant of the formula (I), comprising steps a) and b1) and optionally b2), can be performed in a polar aprotic oil.

This second embodiment (V-II) is particularly suitable for preparation of poly(oxyalkylene)urethane surfactants of the formula (I) as per (A-II), in which R$^2$ is a linear or branched (C$_1$-C$_4$)-alkyl radical which is monosubstituted by carboxyl or N,N-di(methyl)amino, or which is disubstituted by: carboxyl, carboxyl and hydroxyl; or, if X=—O—, R$^2$=[R$^3$—O—CONH—R$^1$—NHCO—O—]$_m$R$^4$ in which R$^3$: —CH$_2$—[C(COOH)(CH$_3$)]—CH$_2$—, R$^4$: C$_2$ to C$_{22}$-alkyl, especially C$_{12}$ to C$_{22}$-alkyl, or a —CH$_2$—[C(COOH)(CH$_3$)]—CH$_2$—OH radical, and m an integer from 1 to 10; where the R$^1$, n, q, and x radicals are each as defined above and the substituents may also be in ionic form.

Suitable polar aprotic oils are, for example, saturated fatty acids and derivatives thereof, such as fatty acid esters and amides, preferably of fatty acids having 8 to 14 carbon atoms, more preferably of fatty acids having 10 to 12 carbon atoms, very particular preference being given to N,N-dimethyldodecanamide, which is commercially available as Agnique AMD 12.

According to (V-II), step a) is performed in a polar aprotic oil and is otherwise as described above for the first embodiment (V-I) of the process.

In the second embodiment of the process (V-II), step b1) is effected generally at a temperature in the range from 20 to 90° C. and is guided especially by the preferably terminally functionalized amine or alcohol used. In step b), the reaction of the preferably terminally functionalized amine with the polyurethane obtained in step a) is effected generally within 20 to 40 minutes. The reaction of the preferably terminally functionalized alcohol with the polyurethane obtained in step a) is effected generally within 2 to 5 hours.

Suitable terminally functionalized amines or alcohols for this second embodiment are especially tertiary amine-containing diols, for example N-methyldiethanolamine (MDEA), or tertiary amine-containing diamines, for example N,N-dimethylethylenediamine, or diols of a tertiary carboxylic acid such as 2,2-dimethylolpropanoic acid (DMPA).

In this second embodiment of the process (V-II), step b1) is advantageously performed in combination with the above-described step b2).

The alkyl alcohol in step b2) is preferably a $(C_{12}-C_{22})$-alkyl alcohol or further alcohol HO—$R^2$ in which the alkyl radical $R^2$ is preferably a di-carboxyl- and -hydroxyl-substituted $(C_1-C_4)$-alkyl radical, for example —$CH_2$—[C(COOH)($CH_3$)]—$CH_2$—OH.

The components from step b2) are preferably added together with the diols from step b1). The proportions of the components are guided by how many diols are desired in the inventive surfactant of the formula (I).

For applications in oil, the inventive poly(oxyalkylene) urethane surfactant obtained after step b1) and/or b2) can be used directly in the polar aprotic oil.

The invention further relates to a composition comprising at least one inventive poly(oxyalkylene)urethane surfactant of the formula (I) and a sparingly water-soluble active ingredient.

The active ingredient is typically soluble in water at 20° C. to an extent of at most 10 g/l, preferably to an extent of at most 2 g/l, more preferably to an extent of at most 0.5 g/l and especially to an extent of at most 0.1 g/l. The composition may comprise one or more different active ingredients. Examples of active ingredients are active agrochemical ingredients, active cosmetic ingredients, active pharmaceutical ingredients or nutrition supplements (such as vitamins and carotenoids). Preferred active ingredients are active pharmaceutical ingredients and active agrochemical ingredients.

Examples of active cosmetic ingredients are cosmetic oils, odorants and aromas, vitamins or UV absorbers. Cosmetic oils include peanut oil, jojoba oil, coconut oil, almond oil, olive oil, palm oil, castor oil, soybean oil, wheatgerm oil, or essential oils such as mountain pine oil, lavender oil, rosemary oil, spruce needle oil, pine needle oil, eucalyptus oil, peppermint oil, sage oil, bergamot oil, turpentine oil, melissa oil, juniper oil, lemon oil, anise oil, cardamom oil, camphor oil, etc., or mixtures thereof. UV absorbers include 2-hydroxy-4-methoxybenzophenone, 2,2',4,4'-tetrahydroxybenzophenone, 2,2'-dihydroxy-4,4'-dimethoxybenzophenone, 2,4-dihydroxybenzophenone, 2'-ethylhexyl 2-cyano-3,3-diphenylacrylate, 2,4,6-trianilino-p-(carbo-2'-ethylhexyl-1'-oxy)-1,3,5-triazine, 3-(4-methoxybenzylidene)camphor, 2-ethylhexyl N, N-dimethyl-4-aminobenzoate, 3,3,5-trimethylcyclohexyl salicylate, 4-isopropyldibenzoylmethane, 2 ethylhexyl p-methoxycinnamate and 2-isoamyl p-methoxycinnamate, and mixtures thereof.

Examples of odorants and aromas are as described in WO 01/49817, or in "Flavors and Fragrances", Ullmann's Encyclopedia of Industrial Chemistry, Wiley-VCH, 2002, to which explicit reference is made.

Examples of vitamins are vitamins, provitamins and vitamin precursors from groups A, C, E and F, especially 3,4-didehydroretinol, beta-carotene (provitamin of vitamin A), ascorbic acid (vitamin C), and the palmitic esters, glucosides or phosphates of ascorbic acid, tocopherols, especially alpha-tocopherol and esters thereof, for example the acetate, the nicotinate, the phosphate and the succinate; and additionally vitamin F, which is understood to mean essential fatty acids, particularly linoleic acid, linolenic acid and arachidonic acid.

Examples of active pharmaceutical ingredients include: benzodiazepines, antihypertensives, vitamins, cytostatics, especially taxol, anesthetics, neuroleptics, antidepressives, antiviral agents, for example anti-HIV agents, antibiotics, antimycotics, antidementia drugs, fungicides, chemotherapeutics, urologics, platelet aggregation inhibitors, sulfonamides, spasmolytics, hormones, immunoglobulins, sera, thyroid therapeutics, psychoactive drugs, Parkinson's drugs and other antihyperkinetics, ophthalmics, neuropathy preparations, calcium metabolism regulators, muscle relaxants, anesthetics, lipid-lowering drugs, hepatotherapeutics, coronary drugs, cardiac drugs, immunotherapeutics, regulatory peptides and inhibitors thereof, hypnotics, sedatives, gynecologicals, gout remedies, fibrinolytics, enzyme preparations and transport proteins, enzyme inhibitors, emetics, blood flow stimulators, diuretics, diagnostic agents, corticoids, cholinergics, biliary therapeutics, antiasthmatics, bronchodilators, beta receptor blockers, calcium antagonists, ACE inhibitors, arteriosclerosis drugs, antiinflammatories, anticoagulants, antihypotensives, antihypoglycemics, antihypertensives, antifibrinolytics, antiepileptics, antiemetics, antidotes, antidiabetics, antiarrhythmics, antianemics, antiallergics, anthelmintics, analgesics, analeptics, aldosterone antagonists, slimming agents.

The term "active agrochemical ingredients" (also referred to hereinafter as pesticides) refers to at least one active ingredient selected from the group of the fungicides, insecticides, nematicides, herbicides, safeners and/or growth regulators. Preferred pesticides are fungicides, insecticides and herbicides, especially fungicides. It is also possible to use mixtures of pesticides from two or more of the aforementioned classes. The person skilled in the art is familiar with such pesticides, which can be found, for example, in Pesticide Manual, 14th ed. (2006), The British Crop Protection Council, London.

Suitable insecticides are insecticides from the class of the carbamates, organophosphates, organochlorine insecticides, phenylpyrazoles, pyrethroids, neonicotinoids, spinosyns, avermectins, milbemycins, juvenile hormone analogs, alkyl halides, organotin compounds, nereistoxin analogs, benzoylureas, diacylhydrazines, METI acaricides, and insecticides such as chloropicrin, pymetrozine, flonicamid, clofentezine, hexythiazox, etoxazole, diafenthiuron, propargite, tetradifon, chlorfenapyr, DNOC, buprofezin, cyromazine, amitraz, hydramethylnon, acequinocyl, fluacrypyrim, rotenone, or derivatives thereof.

Suitable fungicides are fungicides from the classes of dinitroanilines, allylamines, anilinopyrimidines, antibiotics, aromatic hydrocarbons, benzenesulfonamides, benzimidazoles, benzisothiazoles, benzophenones, benzothiadiazoles, benzotriazines, benzyl carbamates, carbamates, carboxamides, chloronitriles, cyanoacetamide oximes, cyanoimidazoles, cyclopropanecarboxamides, dicarboximides, dihydrodioxazines, dinitrophenyl crotonates, dithiocarbamates, dithiolanes, ethyl phosphonates, ethylaminothiazolecarboxamides, guanidines, hydroxy(2-amino)pyrimidines, hydroxyanilides, imidazoles, imidazolinones, inorganics, isobenzofuranones, methoxyacrylates, methoxycarbamates, morpholines, N-phenylcarbamates, oxazolidinediones, oximinoacetates, oximinoacetamides, peptidylpyrimidine nucleosides, phenylacetamides, phenylamides, phenylpyrroles, phenylureas, phosphonates, phosphorothiolates, phthalamic acids, phthalimides, piperazines, piperidines, propionamides, pyridazinones, pyridines, pyridinylmethylbenzamides, pyrimidinamines, pyrimidines, pyrimidinonehydrazones, pyrroloquinolinones, quinazolinones, quinolines, quinones, sulfamides, sulfamoyltriazoles, thiazolecarboxamides, thiocarbamates, thiophanates, thiophenecarboxamides, toluamides, triphenyltin compounds, triazines, triazoles.

Suitable herbicides are herbicides from the classes of the acetamides, amides, aryloxyphenoxypropionates, benzamides, benzofuran, benzoic acids, benzothiadiazinones, bipyridylium, carbamates, chloroacetamides, chlorcarboxylic acids, cyclohexanediones, dinitroanilines, dinitrophenol, diphenyl ethers, glycines, imidazolinones, isoxazoles, isoxazolidinones, nitriles, N-phenylphthalimides, oxadiazoles, oxazolidinediones, oxyacetamides, phenoxycarboxylic acids, phenyl carbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl (thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, ureas.

In one embodiment, the pesticide comprises a fungicide; the pesticide preferably consists of at least one fungicide. A preferred fungicide is fluxapyroxad. In another embodiment, the pesticide comprises a herbicide; the pesticide preferably consists of at least one herbicide. In another embodiment, the pesticide comprises a growth regulator; the pesticide preferably consists of at least one growth regulator.

The inventive composition comprising at least one inventive poly(oxyalkylene)urethane surfactant of the formula (I) and a sparingly water-soluble active ingredient may take the form of a solution, emulsion, suspension or suspoemulsion of the active ingredient. The inventive composition is preferably an aqueous or oily formulation.

"Aqueous" is understood in accordance with the invention to mean that the water content in the formulation is at least 40% by weight. "Oily" is understood in accordance with the invention to mean that the proportion of the overall water-insoluble oil in the formulation is at least 40% by weight.

The invention further provides an aqueous formulation comprising (or consisting of):
i) 0.1 to 25% by weight of at least one poly(oxyalkylene) urethane surfactant of the formula (I), especially according to (A-I),
ii) 0.01 to 20% by weight of at least one sparingly water-soluble active ingredient,
iii) 0 to 40% by weight of at least one water-soluble organic solvent,
iv) 0 to 30% by weight of at least one water-insoluble oil and
v) 40 to 99% by weight of water.

The sum of all the components present in the aqueous formulation adds up to 100% by weight.

Preferably, the aqueous formulation consists of components i) to v).

The aqueous formulation comprises typically 0.01 to 20% by weight of active ingredient, preferably 0.1 to 5% by weight, more preferably 0.2 to 2% by weight, based on the overall composition.

The aqueous formulation comprises typically 0.1 to 25% by weight, preferably 0.5 to 10% by weight, more preferably 1 to 5% by weight, of at least one poly(oxyalkylene)urethane surfactant of the formula (I).

The aqueous formulation preferably comprises at least one poly(oxyalkylene)urethane surfactant of the formula (I) as per the above-described first embodiment (A-I).

The weight ratio of poly(oxyalkylene)urethane surfactant to active ingredient is usually in the range from 1:50 to 100:1, preferably 1:5 to 50:1, more preferably 1:2 to 25:1. The active ingredient may be in dissolved form or in solid, particulate form. The active ingredient particles may be crystalline or amorphous. The particle size may be 1 nm to 10 μm.

Preferably, the aqueous formulation comprises at least 60% by weight, more preferably at least 80% by weight and especially at least 90% by weight of water. Typically, the composition comprises not more than 99% by weight of water.

The invention further provides an oily formulation comprising (or consisting of):
i) 0.1 to 25% by weight of at least one poly(oxyalkylene) urethane surfactant of the formula (I) according to (A-II),
ii) 1 to 50% by weight of at least one sparingly water-soluble active ingredient,
iii) 40 to 98% by weight of at least one water-insoluble oil,
iv) 0 to 30% by weight of at least one water-soluble organic adjuvant, especially of at least one water-soluble organic solvent, and
v) 0 to 10% by weight of water.

The sum of all the components present in the oily formulation adds up to 100% by weight.

Preferably, the oily formulation consists of components i) to v).

The oily formulation comprises typically 0.1 to 50% by weight of active ingredient, preferably 1 to 40% by weight, more preferably 3 to 30% by weight, based on the composition. The oily formulation comprises typically 0.1 to 25% by weight, preferably 0.5 to 10% by weight, more preferably 1 to 5% by weight, of at least one poly(oxyalkylene)urethane surfactant of the formula (I) as per the above-described second embodiment (A-II).

The inventive composition, i.e. either the aqueous formulation or the oily formulation, may comprise formulation auxiliaries, the choice of the auxiliaries typically being guided by the specific use form or active ingredient.

Examples of suitable formulation auxiliaries are solvents, solid carriers, surface-active substances (such as surfactants, protective colloids, wetting agents and tackifiers), organic and inorganic thickeners, bactericides, antifreezes, antifoams, and optionally dyes and stickers (for example for seed treatment).

Useful surface-active substances (adjuvants, wetting agents, tackifiers, dispersants or emulsifiers) include the alkali metal, alkaline earth metal and ammonium salts of aromatic sulfonic acids, for example of lignosulfonic acid (Borresperse® products, Borregaard, Norway), phenolsulfonic acid, naphthalenesulfonic acid (Morwet® products, Akzo Nobel, USA) and dibutylnaphthalenesulfonic acid (Nekal® products, BASF, Germany), and also of fatty acids, alkyl and alkylarylsulfonates, alkyl sulfates, lauryl ether sulfates and fatty alcohol sulfates, and also salts of sulfated hexa-, hepta- and octadecanols, and also of fatty alcohol glycol ethers, condensation products of sulfonated naphthalene and derivatives thereof with formaldehyde, condensation products of naphthalene or of the naphthalenesulfonic acids with phenol and formaldehyde, polyoxyethylene octyl phenol ether, ethoxylated isooctylphenol, octylphenol or nonylphenol, alkylphenyl polyglycol ether, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors, and also proteins, denatured proteins, polysaccharides (e.g. methyl cellulose), hydrophobically modified starches, polyvinyl alcohol (Mowiol® products, Clariant, Switzerland), polycarboxylates (Sokalan® products, BASF, Germany), polyalkoxylates, polyvinylamine (Lupamin® products, BASF, Germany), polyethyleneimine (Lupasol® products, BASF, Germany), polyvinylpyrrolidone and copolymers thereof.

In a preferred embodiment, the active ingredient is an active pharmaceutical ingredient which is used in the inventive composition, especially in the form of an inventive aqueous formulation.

In a further preferred embodiment, the active ingredient is a pesticide and the inventive compositions are in the form of an agrochemical formulation. Suitable agrochemical formulations are water-soluble concentrates (SL, LS), redispersible concentrates (DC), emulsifiable concentrates (EC), emulsions (EW, EO, ES, ME), suspensions (SC, OD, FS) or suspoemulsions (SE). The composition is preferably in the form of an emulsifiable concentrate (EC), of a suspension concentrate (SC), of a of a solution for seed treatment (LS), or of a redispersible concentrate (DC).

The inventive oily formulations in particular are used as emulsifiable concentrates (EC) and suspension concentrates (SC) of an agrochemical formulation.

The inventive aqueous formulations are used as water-soluble concentrates (SL, LS).

The agrochemical formulation is usually diluted before use in order to produce the so-called tankmix. Useful substances for dilution include mineral oil fractions of moderate to high boiling point, such as kerosene or diesel oil, and also coal tar oils and oils of vegetable or animal origin, aliphatic, cyclic and aromatic hydrocarbons, for example toluene, xylene, paraffin, tetrahydronaphthalene, alkylated naphthalenes or derivatives thereof, methanol, ethanol, propanol, butanol, cyclohexanol, cyclohexanone, isophorone, strongly polar solvents, for example dimethyl sulfoxide, N-methylpyrrolidone or water.

Preference is given to using water.

Preferably, the inventive oily formulations are used in the form of an active ingredient concentrate and diluted with water before use.

It is also possible to add the poly(oxyalkylene)urethane surfactant of the formula (I) only to the tankmix. In this embodiment, the inventive composition is in the form of a tankmix.

The diluted composition is typically applied by spraying or nebulization. The following may be added to the tankmix immediately before use: oils of various types, wetting agents, adjuvants, herbicides, bactericides, fungicides. These compositions can be admixed with the compositions according to the invention in a weight ratio of 1:100 to 100:1, preferably 1:10 to 10:1. The pesticide concentration in the tankmix can be varied within relatively wide ranges. It is generally between 0.0001 and 10%, preferably between 0.01 and 1%. According to the type of effect desired, the application rates in the case of use in crop protection are between 0.01 and 2.0 kg of active ingredient per ha.

The invention further relates to a process for preparing the inventive composition, by contacting the inventive poly(oxyalkylene)urethane surfactant of the formula (I) and the active ingredient. The components can be contacted by commonly known methods, such as mixing, emulsifying or suspending.

The invention further relates to the use of the inventive poly(oxyalkylene)urethane surfactants of the formula (I) in an agrochemical formulation comprising the poly(oxyalkylene)urethane surfactant of the formula (I) and a pesticide for control of phytopathogenic fungi and/or unwanted vegetation and/or unwanted insect or mite infestation and/or for regulation of the growth of plants, wherein the formulation is allowed to act on the particular pests, the surroundings thereof or the plants to be protected from the particular pest, the soil and/or on unwanted plants and/or the crop plants and/or the surroundings thereof. In addition, inventive agrochemical formulations can be used for controlling unwanted insects or mite infestation on plants and/or for controlling phytopathogenic fungi and/or for controlling unwanted vegetation, by treating seed of crop plants with the formulation.

The invention further relates to the use of the inventive poly(oxyalkylene)urethane surfactant of the formula (I), especially of that according to (A-I), for solubilizing a sparingly water-soluble active ingredient in aqueous solutions. The active ingredient is preferably soluble in water at 20° C. to an extent of at most 10 g/l. "Solubilization" means that, in the presence of the inventive amphiphile, more active ingredient can be brought into solution than in the absence thereof under otherwise identical conditions. Preferably at least twice the amount, more preferably at least five times and especially ten times the amount can be brought into solution.

In addition, the inventive poly(oxyalkylene)urethane surfactants of the formula (I) can be used as a stabilizer, dispersant, especially as an emulsifier, in aqueous or oily formulations.

The invention further provides for the use of the inventive poly(oxyalkylene)urethane surfactant of the formula (I) as per (A-II) as an oil solubilizer, stabilizer, dispersant, emulsifier or solubilizer of a sparingly water-soluble active ingredient in oily formulations.

Advantages of the present invention are that a high concentration of active ingredient can be brought into solution; that the preparation of the inventive poly(oxyalkylene)urethane surfactant of the formula (I) is possible in a very simple manner and on the industrial scale; and that the inventive poly(oxyalkylene)urethane surfactant of the formula (I) is itself water-soluble or water-dispersible.

The examples which follow are intended to illustrate the invention, without restricting it.

EXAMPLES

Reagents used:
PolyTHF®1000 is a commercial product from BASF (Ludwigshafen, Germany).
Agnique® AMD 12 is a commercial product from BASF.

Example 1

Batch in methyl ethyl ketone (MEK) with solids content 300 g:

75 g of MEK, 0.19 g of DABCO (1,4-diazabicyclo[2.2.2]octane; catalyst) and 234.77 g (0.23 mol) of PolyTHF® 1000 are initially charged in a 3-neck flask and heated to 70° C. Using a dropping funnel, 65.23 g (0.29 mol) of isophorone diisocyanate (IPDI) are added while stirring within 25 minutes. Thereafter, the mixture is heated to 80° C. and polymerized for 2 hours.

The NCO value is then checked (via titration: admix with defined amount of base - back-titration with an acid). If the NCO value is too high, another 0.19 g of DABCO is added and the NCO value is determined regularly until the theoretical value has been attained.

Subsequently, 225 g of MEK are added and the mixture is cooled to 40° C.

Thereafter, 46.42 g of 30% sodium taurinate solution (corresponding to 0.12 mol of taurinate) are added and the mixture is stirred at 40° C. for another hour.

After MEK has been removed by rotary evaporation, the inventive poly(THF)urethane surfactant is dispersed in water, so as to obtain a 30% dispersion in water.

Examples 2 to 6

Examples 2 to 6 were prepared according to example 1, except that the proportions of PTHF and IPDI (examples 2 to 4) or the functionalized amine (examples 5 and 6) were varied according to table 1.

Example 7

Batch in Agnique AMD 12 with solids content 300 g:
75 g of Agnique AMD 12, 0.19 g of DABCO and 175.00 g (0.18 mol) of PolyTHF®1000 were initially charged in a 3-neck flask and heated to 70° C. Using a dropping funnel, 48.62 g (0.22 mol) of IPDI are added while stirring within 25 minutes. Thereafter, the mixture is heated to 80° C. and polymerized for 2 hours. The NCO value is checked and, if necessary, a further 0.19 g of DABCO is added and the mixture is stirred until the theoretical NCO value is attained.

Subsequently, the mixture is cooled to 70° C., 15.65 g (0.12 mol) of dimethylolpropionic acid (DMPA), 31.56 g (0.12 mol) of stearyl alcohol and 0.19 g of DABCO are added, and a dropping funnel is used to add 29.17 g (0.13 mol) of IPDI dropwise over the course of 25 minutes. Thereafter, the mixture is stirred again at 80° C. for a further 2 to 5 h, until no NCO is present any longer. Subsequently, 225 g of Agnique AMD 12 are added. This gives a solution of the inventive poly(THF)urethane surfactant.

Example 8

Batch in Agnique AMD 12 with solids content 300 g:
75 g of Agnique AMD 12, 0.19 g of DABCO and 184.80 g (0.18 mol) of PolyTHF®1000 are initially charged in a 3-neck flask and heated to 70° C. Using a dropping funnel, 51.35 g (0.23 mol) of IPDI are added while stirring within 25 minutes. Thereafter, the mixture is heated to 80° C. and polymerized for 2 hours.

The NCO value is checked and, if necessary, a further 0.19 g of DABCO is added and the mixture is stirred until the theoretical NCO value is attained.

Subsequently, the mixture is cooled to 70° C., 33.05 g (0.25 mol) of dimethylolpropionic acid (DMPA) and 0.19 g of DABCO are added, and a dropping funnel is used to add 30.81 g (0.14 mol) of IPDI dropwise over the course of 25 minutes. Thereafter, the mixture is stirred again at 80° C. for a further 2 to 5 h, until no NCO is present any longer.

Subsequently, 225 g of Agnique AMD 12 are added. This gives a solution of the inventive poly(THF)urethane surfactant.

The inventive poly(oxyalkylene)urethane surfactants of the formula (I) tested are summarized in table 1.

NL=neutralization level

TABLE 1

| Example | Polyurethane block | $NH_2-R^2$ or $HO-R^2$ | Neutralizing agent | Solubility in water (NL 100%) | Solubility in Agnique AMD 12 (NL 100%) |
|---|---|---|---|---|---|
| 1 | 4 mol PTHF (1000 g/mol); 5 mol IPDI | Na taurinate | — | dispersed | — |
| 2 | 2 mol PTHF (2000 g/mol); 3 mol IPDI | Na taurinate | — | dispersed | — |
| 3 | 3 mol PTHF (1000 g/mol); 4 mol IPDI | Na taurinate | — | dispersed | — |
| 4 | 5 mol PTHF (1000 g/mol); 6 mol IPDI | Na taurinate | — | dispersed | — |
| 5 | 4 mol PTHF (1000 g/mol); 5 mol IPDI | Na glycinate | — | dispersed | soluble |
| 6 | 4 mol PTHF (1000 g/mol); 5 mol IPDI | N,N-dimethylethylenediamine | lactic acid or HCl | dispersed | soluble |
| 7 | 4 mol PTHF (1000 g/mol); 5 mol IPDI | DMPA, stearyl alcohol | AMP | dispersed | soluble |
| 8 | 4 mol PTHF (1000 g/mol); 5 mol IPDI | DMPA | AMP | dispersed | soluble |

The inventive neutralized poly(THF)urethane surfactants of examples 1 to 8 are water-dispersible, and those of examples 5 to 8 are additionally soluble in Agnique AMD 12.

X % by weight (X=1, 2.5 or 5% by weight) of poly(THF) urethane surfactant and 2% by weight of active ingredient are dispersed in water. Thereafter, the mixture is stirred for 24 h (magnetic stirrer) and the undissolved active ingredient is filtered off (PVDF syringe filter with pore diameter 0.45 μm).

The solubilization capacities of the inventive poly(THF) urethane surfactants of examples 1, 3 and 4 in water were tested for fenofibrate and fluxapyroxad as sparingly water-soluble active ingredients (table 2). As a comparison, corresponding test results which were obtained with Pluronic 10400 are likewise given in table 2. Pluronic PE 10400 is a poly(a-oxyethylene-b-oxypropylene-a-oxyethylene) triblock copolymer (PEO-PPO-PEO monomer units: 25-56-25) having a molar mass of 5417 g/mol and 40% EO.

TABLE 2

| Surfactant | Surfactant concentration % by weight | Solubilization fenofibrate/ppm | Solubilization fluxapyroxad/ppm |
|---|---|---|---|
| Pluronic 10400 | 1 | 139 | 77 |
| (comparative) | 2.5 | 552 | 289 |
|  | 5 | 1089 | 710 |
| Example 1 | 1 | 747 | 595 |
|  | 2.5 | 1471 | 934 |
|  | 5 | 2896 | 1541 |
| Example 3 | 1 | 646 | 570 |
|  | 2.5 | 1599 | 928 |
|  | 5 | 3242 | 1522 |
| Example 4 | 1 | 748 | 586 |
|  | 2.5 | 1816 | 996 |
|  | 5 | 3584 | 1589 |

In addition, the inventive poly(THF)urethane surfactants according to examples 7 and 8 were used in an oil formulation:

Formulation:
Poly(THF)urethane surfactants: 9% by weight
Active ingredient (fluxapyroxad): 11% by weight
Agnique AMD12: 54.5% by weight
Solvesso: 12.5% by weight
Plurafac LF1300: 11% by weight
Plurafac LF 300: 2% by weight A corresponding formulation with Pluronic PE 10400 is turbid and unstable at room temperature.

The active ingredient was dissolved to give a clear solution in the inventive oily formulation with the poly(THF)urethane surfactants of examples 7 and 8. The inventive formulations are stable even after 72 hours at 0° C.

The results show that the inventive poly(THF)urethane surfactants, compared to the solubilizers known from the prior art, such as Pluronic PE 10400, have much better solubilizing action both in water and in oil.

The invention claimed is:

1. A poly(oxyalkylene)urethane surfactant of the formula (I)

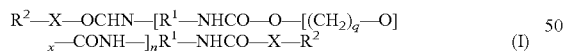
(I)

in which
R$^1$: an alkylene radical, a cycloalkylene radical or an arylene radical;
X: —O— or —NH—;
R$^2$: a linear or branched (C$_1$-C$_4$)-alkyl radical, monosubstituted by a group selected from: sulfo, carboxyl and [N,N-di-(C$_1$-C$_4$)-alkyl]amino, or disubstituted by: carboxyl; carboxyl and hydroxyl; carboxyl and mercapto; or,
if X=—O—, R$^2$ may also be defined as [R$^3$—O—CONH—R$^1$—NHCO—O—]$_m$R$^4$ in which
R$^3$: a linear or branched (C$_1$-C$_4$)-alkylene radical, monosubstituted by COOH,
R$^1$ is as defined above, and
R$^4$: C$_2$-C$_{22}$-alkyl or a —CH$_2$—[C(COOH)(CH$_3$)]—CH$_2$—OH radical, and
m=an integer from 1 to 10;
n=an integer from 1 to 7;
q=an integer from 3 to 5; and
x=an integer from 10 to 70;
or a water-soluble or water-dispersible salt thereof.

2. The poly(oxyalkylene)urethane surfactant of claim 1, wherein, in the formula (I), q=4 and R$^1$ is an alkylene having 4 to 12 carbon atoms or a cycloalkylene having 6 to 12 carbon atoms.

3. The poly(oxyalkylene)urethane surfactant of claim 1, wherein R$^1$ is isophoronediyl.

4. The poly(oxyalkylene)urethane surfactant claim 1, wherein R$^2$ is a linear or branched (C$_1$-C$_4$)-alkyl radical, which is monosubstituted by a group selected from the group consisting of sulfo, carboxyl and [N,N-di-(C$_1$-C$_2$)-alkyl]amino, or which is disubstituted by carboxyl.

5. The poly(oxyalkylene)urethane surfactant of claim 1, wherein R$^2$ is a linear or branched (C$_2$-C$_4$)-alkyl radical which is monosubstituted by carboxyl or N,N-di(methyl)amino, or which is disubstituted by: carboxyl, carboxyl and hydroxyl; or, if X=—O—, R$^2$=[R$^3$—O—CONH—R$^1$—NHCO—O—]$_m$R$^4$ in which
R$^3$: —CH$_2$—[C(COOH)(CH$_3$)]—CH$_2$—,
R$^4$: C$_2$ to C$_{22}$-alkyl or a —CH$_2$—[C(COOH)(CH$_3$)]—CH$_2$—OH radical, and
m=1 to 5.

6. A process for preparing the poly(oxyalkylene)urethane surfactant of formula (I) of claim 1, comprising
a) reacting at least one diisocyanate OCN—R$^1$—NCO with at least one polyetherdiol HO—[(CH$_2$)$_q$—O]$_x$—H in a polar aprotic solvent to give a polyurethane; and
b1) reacting the polyurethane obtained with an optionally terminally functionalized amine or alcohol of the formula NH$_2$—R$^2$ or HO—R$^2$, and
b2) optionally, if the alkyl radical R$^2$ of the alcohol HO—R$^2$ is a di-carboxyl- and -hydroxyl-substituted (C$_1$-C$_4$)-alkyl radical, reacting the functionalized polyurethane with further diisocyanate OCN—R$^1$—NCO and an alkyl alcohol.

7. The process of claim 6, wherein the polar aprotic solvent used is a polar aprotic oil of a fatty acid ester or fatty acid amide of saturated fatty acids.

8. A composition comprising the poly(oxyalkylene)urethane surfactant of claim 1 and a sparingly water-soluble active ingredient having a water-solubility of at most 10 g/l at 20° C.

9. The composition of claim 8 comprising:
i) 0.1 to 25% by weight of the poly(oxyalkylene)urethane surfactant,
ii) 0.01 to 20% by weight of the sparingly water-soluble active ingredient having a water-solubility of at most 10 g/l at 20° C.,
iii) 0 to 30% by weight of at least one water-insoluble oil and
iv) 40 to 99% by weight of water.

10. The composition of claim 8 comprising:
i) 0.1 to 25% by weight of the poly(oxyalkylene)urethane surfactant
ii) 1 to 50% by weight of the sparingly water-soluble active ingredient having a water-solubility of at most 10 g/l at 20° C.,
iii) 40 to 98% by weight of at least one water-insoluble oil, and
iv) 0 to 10% by weight of water.

11. A method for controlling phytopathogenic fungi, unwanted vegetation, or unwanted insect or mite infestation or for regulating growth of plants comprising allowing a formulation comprising the poly(oxyalkylene)urethane surfactant of claim 1 to act on the insect or mite or the surroundings thereof on plants to be protected from the fungi, insect or mite or the soil surroundings.

12. A seed treated with a composition comprising the poly(oxyalkylene)urethane surfactant of claim 1.

13. The poly(oxyalkylene)urethane surfactant of claim 4, wherein X=—NH—, q=4,
   $R^1$=isophoronediyl, n=1 to 7, x=13 to 28 and
   $R^2$ is one of the following moieties: sulfonato-2-ethyl, carboxymethyl, carboxylatomethyl, 1,2-dicarboxylatoethyl, N,N-dimethyl-2-aminoethyl and the ammonium ion thereof.

14. The poly(oxyalkylene)urethane surfactant of claim 5, wherein q=4, $R^1$=isophoronediyl, n=1 to 7, x=13 to 28, X=O, $R^2$ is —$CH_2$—[C(COOH)($CH_3$)]—$CH_2$—OH or [$R^3$—O—CONH—$R^1$—NHCO—O—]$_m R^4$ in which m=1 to 3, $R^4$=$C_{12}$-$C_{22}$-alkyl or a —$CH_2$—[C(COOH)($CH_3$)]—$CH_2$—OH radical and $R^3$ is a linear or branched ($C_1$-$C_4$)-alkylene radical, monosubstituted by COOH.

15. The seed of claim 12, wherein, in the formula (I), q=4 and $R^1$ is an alkylene having 4 to 12 carbon atoms or a cycloalkylene having 6 to 12 carbon atoms.

16. The seed of claim 12, wherein, $R^1$ is isophoronediyl.

17. The method of claim 11, wherein, in the formula (I), q=4 and $R^1$ is an alkylene having 4 to 12 carbon atoms or a cycloalkylene having 6 to 12 carbon atoms.

18. The method of claim 11, wherein, $R^1$ is isophoronediyl.

19. The method of claim 11, wherein, $R^2$ is a linear or branched ($C_1$-$C_4$)-alkyl radical, which is monosubstituted by a group selected from the group consisting of sulfo, carboxyl and [N,N-di-($C_1$-$C_2$)-alkyl]amino, or which is disubstituted by carboxyl.

20. The method of claim 11, wherein, $R^2$ is a linear or branched ($C_2$-$C_4$)-alkyl radical which is monosubstituted by carboxyl or N,N-di(methyl)amino, or which is disubstituted by: carboxyl, carboxyl and hydroxyl; or, if X=—O—, $R^2$= [$R^3$—O—CONH—$R^1$—NHCO—O—]$_m R^4$ in which
   $R^3$: —$CH_2$—[C(COOH)($CH_3$)]—$CH_2$—,
   $R^4$: $C_2$ to $C_{22}$-alkyl or a —$CH_2$—[C(COOH)($CH_3$)]—$CH_2$—OH radical, and
   m=1 to 5.

* * * * *